United States Patent [19]

Moscovici et al.

[11] Patent Number: 5,338,680
[45] Date of Patent: Aug. 16, 1994

[54] NON-PRODUCER CELL LINES TRANSFORMED BY AMV

[76] Inventors: Carlo Moscovici; M. Giovannella Moscovici, both of 6816 NW. 18th Ave., Gainsville, Fla. 32605

[21] Appl. No.: 109,107

[22] Filed: Aug. 19, 1993

Related U.S. Application Data

[63] Continuation of Ser. No. 802,711, Dec. 6, 1991, abandoned, which is a continuation of Ser. No. 529,623, May 29, 1990, abandoned.

[51] Int. Cl.$^5$ .................. C12N 5/00; C12N 15/00
[52] U.S. Cl. .................. 435/240.2; 435/172.3
[58] Field of Search .................. 435/240.2, 172.3

[56] References Cited

PUBLICATIONS

Moscovici et al., In Vivo and In Vitro Erythropoiesis: The Friend System, G. B. Rossi, ed. (Amsterdam: Elsevier-North Holland) pp. 503–514 (1980).
Duesberg, et al., Proc. Natl. Acad. Sci. USA, 77:5120–5124 (1980).
Gonda, et al., Cell, 23:279–290 (1981).
Klempnauer, et al., Cell, 33:345–355 (1983).
Moscovici et al., Expression of Differentiated Functions in Cancer Cells, R. F. Revoltella et al., eds. (New York:Raven Press) pp. 435–449 (1982).
Klempnauer, et al., Cell: 37, 537–547 (1984).
Symonds, et al., Mol. and Cell. Biol. :4, 2587–2593 (1984).
Ghysdael, et al., EMBO: 5, 2251–2256, (1986).
Rosson & Virology 175(2):562–567, 1990.
Moscovici et al. *In vivo & In Vitro Erythropiesis: The Friend System*, pp. 503–514 1980.
Rosbe et al. Cell 31: 643, 1982.
Symonds et al. Mol. Cell Biol. 4(12):2587 1984.
Klempnauer et al. Cell 33:345 1985.

*Primary Examiner*—Suzanne E. Ziska
*Attorney, Agent, or Firm*—Beveridge, DeGrandi, Weilacher & Young

[57] ABSTRACT

AMV-transformed non-producer cells lines which may be grown in chicken serum-free media are disclosed. These cells have been transformed with the avian myeloblastosis virus oncogene, and are capable of being grown without chicken serum.

1 Claim, No Drawings

NON-PRODUCER CELL LINES TRANSFORMED BY AMV

This application is a continuation, of application Ser. No. 07/802,711, filed Dec. 6, 1991, now abandoned which application is entirely incorporated herein by reference and which in turn is a continuation of application Ser. No. 07/529,623 filed May 29, 1990, now abandoned.

BACKGROUND OF THE INVENTION

Avian myeloblastosis virus (AMV) induces an acute myeloblastic leukemia in birds and is capable of transforming myeloid hematopoietic cells in vitro. AMV is a replication-defective virus and therefore requires a helper virus for replication.

Some of the features of this virus include: it is replication-defective; it is able to transform cells of hemopoietic origin (except fibroblast cells) together with cells of connective tissue origin; and finally it can induce leukemia in the chicken after short periods of latency.

Previous experiments have shown that after infection of hemopoietic cells with AMV, it is possible to obtain continuous lines of nonadherent transformed cells that can permanently release infectious virus. These cells are also found to carry distinctive markers of myeloid differentiations.

SUMMARY OF THE INVENTION

Cell lines according to the present invention are non-producer arian cells transformed by avian myeloblastosis virus, and are capable of being grown in media which does not include chicken serum or phosphate. These cells are particularly suited for the production of arian vaccines.

STATEMENT OF DEPOSIT

Cell lines according to the present invention have been deposited in the American Type Culture Collection at 12301 Parklawn Drive, Rockville, Md. 20852-1776 on May 25, 1990, thus affording permanency of the deposit and ready availability to the public upon issuance of a patent. Cell line BM2L has received ATCC No. CRL10468; cell line BM2L/A$_1$b$_6$ (also known as GM1243/1) has received ATCC No. CRL10465; cell line BM2L/A$_2$a2 (also known as GM1243/2) has received ATCC No. CRL10466; :; and cell line BM2L/A$_2$5 (also known as GM1243/3) has received ATCC No. CRL10467.

DESCRIPTION OF THE PREFERRED EMBODIMENT

The present invention comprises an immortalized or continuous cell line of non-producer chicken cells transformed by avian myeloblastosis virus (AMV). In a preferred embodiment, a cell line of the invention grows in a culture media in the absence of tryptose phosphate broth and chicken serum.

Non-producer clones of myeloblasts transformed by AMV are known [Moscovici, et al., *In Vivo and In Vitro Erythropoiesis: The Friend System*, G.B. Rossi, ed. (Amsterdam: Elsevier-North Holland), pp. 503–514 (1980)]. A non-producer cell line GM 727, a myeloblastic cell line originating from SPAFAS embryonic bone marrow cells infected with AMV, were prepared in soft agar and developed into colonies. The GM 727 cells exhibit characteristics of monoblasts: they are positive for Fc receptors, can phagocytize latex particles, are negative for complement receptors and immune phagocytosis, and produce colonies indistinguishable from AMV producer monoblasts in soft agar. Some virus-specific products are made by these cells, and infectious virions were never detected by the reverse transcriptase assay or conventional biological assays.

Supernatant fluids from actively growing colonies of GM 727 were tested for production of virus by reverse transcriptase and conventional biological assays, such as transforming assay and the plaque assay. The BM2 cell line originated from the recovery of cells from the bone marrow of a bird injected in ovum with GM 727.

Typically, transformation of cells such as monoblasts, using viral agents such as AMV, is accomplished by flushing bone marrow out of chicken tibias, dispersing the cells in medium by vigorous pipetting, passing the cells through a fine mesh nylon cloth in order to obtain a single cell suspension, and then infecting the single cell suspension with the viral transformant. Colonies of cells transformed by AMV are easily recognizable morphologically using phase contrast microscopy, or by reverse transcriptase and conventional biological assays, such as transforming assay and the plaque assay.

Thereafter, the transformed monoblasts are serially sub-cultured to select the stably transformed cells from abortive or transiently transformed cells. The stable cells may then used to establish a line for use in accordance with the present invention. Specific details of a preferred transformation procedure are set forth in the Examples below.

In accordance with the present invention, bone marrow cells, preferably from a chicken embryo, are infected with arian myeloblastosis virus, resulting in the production of a transformed cell line. Infection typically occurs by culturing the bone marrow cells with AMV. Included within the scope of the invention is culturing hematopoietic chicken cells with AMV, or a portion thereof, such as the v-myb or c-myb genes. Duesberg, et al., PNAS, 77:5120–5124 (1980) and Gonda, et al., CELL, 23:279-290 (1981) [both herein incorporated by reference] disclose the genetic structure of AMV. The AMV oncogene, v-myb, and a plasmid which may be used for the expression of the oncogene, are disclosed in Klempnauer, et al., Cell, 33:345–355 (1983), and is also herein incorporated by reference. Preferred transformed cells are disclosed in the Moscovici, et al. publication cited above.

In a preferred embodiment, BM2 cells, an AMV-transformed non-producer cell line [described in Moscovici, et al., *Expression of Differentiated Functions in Cancer Cells*, R.F. Revoltella et al., eds. (New York: Raven Press) pp. 435–449 (1982), herein incorporated by reference] were used to produce cells capable of being cultured in chicken serum-free media. The GM 727 cell line was produced from GM 727 cells, as described in Example 1. The BM2L cell line was produced according to Example 2, and was used to produce GM 1243/1, GM1243/2, and GM 1243/3, as described in Example 3.

Incubation of the parental cells according to the present invention is typically conducted in the presence of a nutrient medium which maintains the cells at temperatures permitting propagation of the virus in the cell culture. Typically, such temperatures are from about 33° C. to about 39° C., preferably about 37° C. The nutrient medium may be, for example, Eagle's Minimum Essential Medium (EMEM), Williams Medium E, Medium 199, Dulbecco's Modified Eagle's Medium, Roswell Park Memorial Institute culture media (RPMI-1640) or Basal Medium Eagle with, for BM2 and BM2L cells, chicken serum, tryptose phosphate broth, and calf (preferably newborn) serum. Other equivalent media may be used as well. The medium may contain a sufficient quantity of a buffering agent, such as sodium hydrogencarbonate, to maintain a stable pH. Other ingredients such as folic acid may be added to the culture medium in order to promote cell growth, particularly cell growth in suspension. Antibiotics, such as gentamycin, penicillin, streptomycin, and the like are advantageously included in order to prevent bacterial and/or fungal contamination of the culture. Typical media are shown in Example 4.

In a preferred embodiment, the cell lines according to the present invention—BM2L/$A_1b_6$, BM2L/$A_2a2$, and BM2L/$A_2b_5$, and their progeny, clones, variants, and mutations—are grown in a medium such as one of those noted above, but which does not contain chicken serum or a phosphate such as tryptose phosphate. Such serum-free cells may be typically maintained in serum-free medium for about 48 hours. In a preferred embodiment, if long term maintenance is desired, a non-chicken serum, such as newborn calf serum, may be added.

The invention extends to the use of the serum-independent avian cell lines according to the present invention for the preparation of biologically active compounds or vaccines under serum-free conditions.

The terms "immortalized" or "continuous" as used herein means that the cell line grows continually without senescence when cultured in vitro in a suitable growth medium.

"Non-producer" as used herein refers to cells which do not release infectious virus. Typically, non-producer cells contain AMV viral sequences but do not contain the genome of the helper virus.

The term "serum-free medium" as used herein refers to a medium which is deprived of chicken serum, and/or a phosphate, such as tryptose phosphate. Chicken vaccines produced using the serum-free cell lines of the present invention do not include the contaminants normally associated with chicken serum.

A transformed cell line, i.e., cells which have been infected by AMV, may be detected in vivo by growing the cells infected with the virus in one of several selective media. The labeling procedure typically includes culturing non-producer cells in a selective medium which contains $^{125}$I-iodo-2-deoxyuridine ($^{125}$IUDR), a labelled nucleoside which can be radioactively measured, and Tris buffer. SPAFAS embryonic bone marrow cells transformed with AMV are cultured in a $^{125}$IUDR medium and the percentage of labelled cells can be determined by autoradiography. Labelled cells are those containing whole provirus DNA in the living cell. Other methodologies for detecting the transformed cells in vivo include tagging the cells with beta-galactosidase.

Advantages of the cell lines include an enormous reduction is costs since serum is very expensive; cheap and simple purification of products produced by the new cell lines because there are no serum contaminants and because product can be easily purified from serum-free medium; the possibility of producing proteins which, due to the presence of proteases in serum, cannot be obtained, or can only be obtained in small quantities, from serum-dependent cell lines.

Utility of cell Lines

1) Production of chicken-serum free vaccines: the production of chicken vaccines using a continuous cell line which grows without chicken serum is significantly easier and much less costly because all that is needed is a cell suspension and an infecting agent (a chicken cytopathic virus or virus, for example). Advantages include large volume production of vaccine at a relatively small cost. Some of these vaccines include, but are not limited to, Newcastle's disease, Fowl Pox, avian encephalomyelitis and arian infectious bronchitis.

2) Identification of potential therapeutic drugs or vaccines: These cells are useful for screening drugs or vaccines for the treatment of leukemia and related diseases, by growing the cells in media which contains the vaccine and then determining extent cytotoxicity occurs, e.g., trypan blue exclusion assay or related assays, or by growth assays such as colony forming efficiency, all of which are standard techniques well known in the art.

3) Studies of chromosome damaging agents: substances known or suspected of causing chromosomal damage may be added to a culture medium containing these cells, and then the extent of chromosomal damage can be measured.

4) Studies of malignant transformation by vital agents and transferred genes, including oncogenes, using standard assays such as anchorage independent growth or tumor formation.

5) Use of cells altered by transfer of oncogenes of paragraph 3 above to screen for potential therapeutic agents by the techniques noted in paragraph 1 above, particularly for cells transformed by the activation of certain oncogenes or combination of oncogenes.

6) Studies of cellular biochemistry, particularly those related to cell growth and the action of exogenous agents (such as those described in paragraphs 1–4 above).

7) Studies of cellular responses to growth factors and production of growth factors. These cells are particularly useful for such applications because they grow in defined growth media such as chicken-serum free and phosphate free media.

8) A model for the study of metastasis: the biological regulation of metastasis has not yet been determined or elucidated. The metastasis puzzle is what triggers a non-metastatic cell to become metastatic. By comparing the BM2 cell line (which remains in the bone marrow in Vivo) to the BM2L cell line (which migrates in vivo through the blood stream to other organs and tissues), information about the cellular or molecular changes in a metastatic cell may be determined.

While the invention is susceptible to various modifications and alternative forms, certain specific embodiments thereof are described in the examples set forth below. It should be understood, however, that these examples are not intended to limit the invention to the particular embodiments disclosed, but, on the contrary, the intention is to cover all modifications, equivalents, and alternatives falling within the spirit and scope of the invention.

In order that the invention herein described may be more fully understood, the following examples are for illustrative purposes only and are not to be construed as limiting this invention in any manner.

Examples

EXAMPLE 1. Development of the parental GM 727 cell line

Bone marrow cultures were prepared from birds (baby chick SPAFAS) injected with NPs. The tibias were freed of all muscle and membranes and rinsed three times with Tris buffer. The cells were obtained by flushing media through the bone marrow with a syringe. The cell clumps were broken up by pipetting and were passed through a nylon cloth in order to produce a single cell suspension. $1 \times 10^6$ of the cell suspension was then resuspended in 0.5 ml serial dilutions of biologically cloned AMV (MAV-2). Viral adsorption was carried out for 30 minutes at $+4°$ C. followed by 30 minutes at room temperature. Infected cells were then seeded at $5 \times 10^4$ per 35 mm dish, incubated at $37.5°$ C. in 5% $CO_2$ and colonies were scored and picked 10 days later.

Individual colonies were picked and seeded into multi-well plates and propagated in growth medium. The NP AMV myeloblasts were grown at a density of $6-10 \times 10^6$ cells/ml in BT-88(4) medium plus 160 μg/100 ml of folic acid. Supernatant fluids from individual colonies were harvested, filtered and tested for presence or absence of virus release by reverse transcriptase assay and by transformation assays of susceptible target cells.

Transformed non-producer monoblast cells were obtained from solitary infection of cells with the $10^{-3}$ virus shock dilution.

One non-producer clonal population was selected and labelled GM727.

$1 \times 10^6$ GM727 cells suspended in 100 μl medium were injected into the chorion allantoic membrane vein of 12 day old chicken embryos.

After hatching, chickens were monitored for onset of leukemia by blood smears twice a week. All experimental chicken remained leukemia negative. Once a week individual birds were sacrificed and their respective bone marrows were cultured in vitro. Monoblastic transformed cells were consistently reisolated from 1 week, 2 week, 3 week, and 4 week birds. From a 2 week old chick bone marrow, transformed cells were reisolated and a continuous line was obtained and named BM2. Cells from BM2 were cloned and one clone was selected and labelled BM2 $C_3A$.

The continuous BM2 $C_3A$ cell line and its progeny has maintained its phenotype, biological properties, and lack of leukemogenicity for many years making it a unique chicken line.

EXAMPLE 2. Development of the BM2L cell line

A chicken injected with BM2/$C_3A$ showed anemia accompanied by runting. The bird was immediately sacrificed and autopsied.

Macroscopical and microscopical examination revealed microtumors in spleen, liver, heart, and bone marrow. The hystopath confirmed a leukemic process.

Leukemic bone marrow cells were cultured in vitro. The cells grew very actively with a generation time of 48 hours.

The cells were subcloned, and two clonal populations selected, and labelled BM2/$LA_1$, and BM2/$LA_2$, respectively. Supernatent fluids from the above cultures were collected and tested by reverse transcriptase assay, which indicated that they were still non-producer.

DNA analysis by Southern Blot of BM2 $C_3A$, BM2/$LA_1$ and BM2/$LA_2$ cells showed no detectable change in the "v-myb" gene of AMV.

Moreover, BM2/$LA_1$ when reinjected in chicken embryo again caused acute leukemia.

EXAMPLE 3

Clonal populations of BM2/L can be grown in the absence of tryptose phosphate broth and chicken serum. Serial dilutions of cells BM2/$LA_1$ and BM2/$LA_2$ were seeded in soft agar medium composed as follows:

| Agar Medium | |
|---|---|
| F-12 (2x) | 20% |
| F-12 (1x) | 10% |
| Fetal bovine serum | 10% |
| Dulbecco modified medium 1x | 40% |
| Vitamin 100x | 1% |
| Folic Acid 100x | 1% |
| Gentamycin | |
| Growth Medium | |
| Dulbecco modified medium 1x | 88% |
| Newborn calf serum | 10% |
| Vitamin 100x | 1% |
| Folic acid 100x | 1% |
| Gentamycin | |
| pH | 7.2 |

Colonies were picked 10 days later from cultures seeded at $1 \times 10^3$ cells/35 mm dish and propagated in growth medium. Cell progenies from three colonies were selected, i.e., GM 1243/1, GM1243/2, and GM 1243/3.

| F12 OVERLAY | 20 ml | 30 ml | 40 ml | 50 ml | 60 ml | 70 ml | 80 ml | 90 ml | 100 ml |
|---|---|---|---|---|---|---|---|---|---|
| F12 (2X) | 4.0 | 6.0 | 8.0 | 10.0 | 12.0 | 14.0 | 16.0 | 18.0 | 20.0 |
| Calf Serum | 1.2 | 1.8 | 2.4 | 3.0 | 3.6 | 4.2 | 4.8 | 5.4 | 6.0 |
| Chicken Serum | 0.4 | 0.6 | 0.8 | 1.0 | 1.2 | 1.4 | 1.6 | 1.8 | 2.0 |
| Tryptose Phosphate | 2.0 | 3.0 | 4.0 | 5.0 | 6.0 | 7.0 | 8.0 | 9.0 | 10.0 |
| 100X Vitamins | 0.2 | 0.3 | 0.4 | 0.5 | 0.6 | 0.7 | 0.8 | 0.9 | 1.0 |
| 100X Folic Acid | 0.2 | 0.3 | 0.4 | 0.5 | 0.6 | 0.7 | 0.8 | 0.9 | 1.0 |
| Conditioned Medium* | 8.0 | 12.0 | 16.0 | 20.0 | 24.0 | 28.0 | 32.0 | 36.0 | 40.0 |
| Gentamycin Bacto Agar (3.6%) or (1.8%) | 4.0 | 6.0 | 8.0 | 10.0 | 12.0 | 14.0 | 16.0 | 18.0 | 20.0 |

*Conditioned Medium: Consisting of supernatant fluids of primary chicken embryo cells (from 9 day old embryo) after 4 days in culture.

Dulbecco'3 s Modified Eagle Medium

Base Medium 1-liter package of Dulbecco's Modified Eagle Medium powder obtained from GIBCO—Formula #78-5440, to which may be added 2.2 g of $NaHCO_3$ and 1 liter of water, filter sterilize and aliquot into sterile bottles.

| Complete Medium | |
| --- | --- |
| Dulbecco's Modified Eagle Medium | 80 ml |
| Tryptose Phosphate Broth (29.5 g/l) | 10 ml |
| Calf Serum | 5 ml |
| Chicken Serum (heat inactivated) | 5 ml |
| Gentamicin (10 mg/ml) | 0.1 ml |

Although the foregoing invention has been described in some detail by way of illustration and example, it should be understood that the invention is not limited thereto, and that many obvious modifications and variations thereof can be made, and that such modifications are intended to fall within the scope of the appended claims.

What is claimed is:

1. A cell line consisting essentially of chicken cells selected from the group consisting of ATCC CRL 10465, and progeny thereof; ATCC CRL 10466, and progeny thereof; ATCC CRL 10467, and progeny thereof; and ATCC CRL 10468, and progeny thereof; which cell line is capable of being cultured and maintained in a culture medium free of chicken serum and free of tryptose phosphate.

* * * * *